United States Patent
Nielsen

(10) Patent No.: US 10,335,428 B2
(45) Date of Patent: *Jul. 2, 2019

(54) P-ETHOXY NUCLEIC ACIDS FOR LIPOSOMAL FORMULATION

(71) Applicant: Bio-Path Holdings, Inc., Bellaire, TX (US)

(72) Inventor: Peter Nielsen, Katy, TX (US)

(73) Assignee: BIO-PATH HOLDINGS, INC., Bellaire, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/657,083

(22) Filed: Jul. 21, 2017

(65) Prior Publication Data

US 2018/0161360 A1  Jun. 14, 2018

Related U.S. Application Data

(63) Continuation of application No. 15/294,223, filed on Oct. 14, 2016, now Pat. No. 9,744,187.

(60) Provisional application No. 62/241,503, filed on Oct. 14, 2015.

(51) Int. Cl.
| | |
|---|---|
| *A61K 31/7125* | (2006.01) |
| *C12N 15/113* | (2010.01) |
| *A61K 47/69* | (2017.01) |
| *A61K 47/54* | (2017.01) |
| *C12N 15/11* | (2006.01) |

(52) U.S. Cl.
CPC ........ *A61K 31/7125* (2013.01); *A61K 47/544* (2017.08); *A61K 47/548* (2017.08); *A61K 47/6911* (2017.08); *C12N 15/111* (2013.01); *C12N 15/113* (2013.01); *C12N 2310/11* (2013.01); *C12N 2310/113* (2013.01); *C12N 2310/31* (2013.01); *C12N 2320/32* (2013.01); *Y02A 50/473* (2018.01); *Y02A 50/478* (2018.01)

(58) Field of Classification Search
None
See application file for complete search history.

(56) References Cited

U.S. PATENT DOCUMENTS

| | | |
|---|---|---|
| 5,087,617 A | 2/1992 | Smith |
| 5,248,671 A | 9/1993 | Smith |
| 5,567,433 A | 10/1996 | Collins |
| 5,855,911 A | 1/1999 | Lopez-Berestein |
| 6,015,886 A | 1/2000 | Dale et al. |
| 6,042,846 A | 3/2000 | Lopez-Berestein |
| 6,111,094 A | 8/2000 | Bennett |
| 6,977,244 B2 | 12/2005 | Tormo et al. |
| 7,176,302 B2 | 2/2007 | Lopez-Berestein |
| 7,220,853 B2 | 5/2007 | Lopez-Berestein et al. |
| 7,285,288 B1 | 10/2007 | Tormo et al. |
| 7,309,692 B1 | 12/2007 | Lopez-Berestein et al. |
| 7,425,545 B2 | 9/2008 | Crooke |
| 7,704,962 B1 | 4/2010 | Tari et al. |
| 7,754,872 B2 | 7/2010 | Lopez-Berestein |
| 7,923,548 B2 | 4/2011 | Lopez-Berestein et al. |
| 2003/0176376 A1* | 9/2003 | Klem .................. C12N 15/113 514/44 R |
| 2005/0186264 A1 | 8/2005 | Kiani |
| 2007/0190382 A1 | 3/2007 | Esau |
| 2008/0171718 A1* | 7/2008 | Brown ................ A61K 31/282 514/44 A |
| 2011/0190382 A1 | 8/2011 | Gleave |
| 2014/0121262 A1 | 5/2014 | Feinberg |

FOREIGN PATENT DOCUMENTS

| | | |
|---|---|---|
| WO | WO 97/07784 | 3/1997 |
| WO | WO 01/60998 | 8/2001 |

OTHER PUBLICATIONS

Gutierrez-Puente et al., "Cellular pharmacology of p-ethoxy antisense oligonucleotides targeted to Bcl-2 in a follicular lymphoma cell line", *Leukemia & Lymphoma*, 44(11): 1979-1985, 2003.
International Search Report and Written Opinion issued in International Application No. PCT/US2016/057148, dated Jan. 18, 2017.

* cited by examiner

*Primary Examiner* — Tracy Vivlemore
(74) *Attorney, Agent, or Firm* — Parker Highlander PLLC

(57) ABSTRACT

Provided herein are therapeutic oligonucleotides that comprise at least one p-ethoxy backbone linkage but no more than 80% p-ethoxy backbone linkages. Provided herein are improved delivery systems for therapeutic oligonucleotides comprising a liposome that comprises neutral phospholipids and a p-ethoxy oligonucleotide that is entrapped in the liposome.

20 Claims, No Drawings

P-ETHOXY NUCLEIC ACIDS FOR LIPOSOMAL FORMULATION

The present application is a continuation of U.S. application Ser. No. 15/294,223, filed Oct. 14, 2016, which claims the priority benefit of U.S. provisional application No. 62/241,503, filed Oct. 14, 2015, the entire contents of each of which are incorporated herein by reference.

BACKGROUND OF THE INVENTION

1. Field of the Invention

The present invention relates generally to the field of medicine. More particularly, it concerns liposomal formulations of p-ethoxy oligonucleotides and methods of making and using such formulations in medicine.

2. Description of Related Art

Antisense oligonucleotides (oligos) complementary to specific regions of a target mRNA have been used to inhibit the expression of endogenous genes. When the antisense oligonucleotides bind to a target mRNA, a DNA-RNA hybrid is formed. This hybrid formation inhibits the translation of the mRNA and, thus, the expression of the encoded protein. If the protein is essential for the survival of the cell, the inhibition of its expression may lead to cell death. Therefore, antisense oligonucleotides can be useful tools in anticancer and antiviral therapies.

The main obstacles in using antisense oligonucleotides to inhibit gene expression are cellular instability, low cellular uptake, and poor intercellular delivery. Natural phosphodiesters are not resistant to nuclease hydrolysis; thus high concentrations of antisense oligonucleotides are needed before any inhibitory effect is observed. Modified phosphodiester analogs, such as p-ethoxy, have been made to overcome this nuclease hydrolysis problem, but they have not provided a satisfactory solution to the problem.

The cellular uptake of antisense oligonucleotides is low. To solve this problem, physical techniques, such as calcium-phosphate precipitation, DEAE-dextran mediation, or electroporation, have been used to increase the cellular uptake of oligonucleotides. These techniques are difficult to reproduce and are inapplicable in vivo. Cationic lipids, such as Lipofectin, have also been used to deliver oligonucleotides. An electrostatic interaction is formed between the cationic lipids and the negatively charged oligonucleotides, which results in a complex that is then taken up by the target cells. Since these cationic lipids do not protect the oligonucleotides from nuclease digestion, are harmful to the cell membrane, and they are only useful in delivering the nuclease-resistant phosphorothioates, but not the nuclease-cleavable phosphodiesters.

Another modified phosphodiester (PD) analog that has been prepared is p-ethoxy (pE) oligos. The modifications of pE oligos are made in the phosphate backbone so that the modification will not interfere with the binding of these oligos to a target mRNA. pE oligos are made by adding an ethyl group to the non-bridging oxygen atom of the phosphate backbone, thus rendering these oligos uncharged compounds. In spite of their resistance to nucleases, the cellular uptake and intracellular delivery of pE oligos is poor because upon internalization, these oligos remain sequestered inside the endosomal/lysosomal vacuoles, impeding their access to target mRNA.

There is a need for improved antisense compositions for use in treatment of disease, and also a need for processes for making such improved compositions.

SUMMARY OF THE INVENTION

In one embodiment, compositions are provided comprising a population of oligonucleotides. In some aspects, the oligonucleotides of the population are composed of nucleoside molecules linked together through phosphate backbone linkages, wherein at least one of the phosphate backbone linkages in each oligonucleotide is a p-ethoxy backbone linkage, and wherein no more than 80% of the phosphate backbone linkages in each oligonucleotide are p-ethoxy backbone linkages. In some aspects, at least one of the phosphate backbone linkages in each oligonucleotide is a phosphodiester backbone linkage. In some aspects, 10% to 80% of the phosphate backbone linkages are p-ethoxy backbone linkages; 20% to 80% of the phosphate backbone linkages are p-ethoxy backbone linkages; 30% to 80% of the phosphate backbone linkages are p-ethoxy backbone linkages; 40% to 80% of the phosphate backbone linkages are p-ethoxy backbone linkages; 50% to 80% of the phosphate backbone linkages are p-ethoxy backbone linkages; or 60% to 70% of the phosphate backbone linkages are p-ethoxy backbone linkages, or any range derivable therein. In some aspects, 20% to 90% of the phosphate backbone linkages are phosphodiester backbone linkages; 20% to 80% of the phosphate backbone linkages are phosphodiester backbone linkages; 20% to 70% of the phosphate backbone linkages are phosphodiester backbone linkages; 20% to 60% of the phosphate backbone linkages are phosphodiester backbone linkages; 20% to 50% of the phosphate backbone linkages are phosphodiester backbone linkages; or 30% to 40% of the phosphate backbone linkages are phosphodiester backbone linkages, or any range derivable therein. In various aspects, at least 5%, 10%, 15%, 20%, 25%, 30%, 35%, 40%, 45%, 50%, 55%, 60%, 65%, 60%, 65%, 70%, 75%, 80%, 85%, 90%, or 95%, or any value therein, of the phosphate backbone linkages are p-ethoxy backbone linkages. In various aspects, at most 5%, 10%, 15%, 20%, 25%, 30%, 35%, 40%, 45%, 50%, 55%, 60%, 65%, 70%, 75%, 80%, 85%, 90%, or 95%, or any value therein, of the phosphate backbone linkages are phosphodiester backbone linkages. In some aspects, the composition is lyophilized.

In some aspects, the oligonucleotides of the population have a size ranging from 7 to 30 nucleotides. In certain aspects, the oligonucleotides of the population have a size ranging from 12 to 25 nucleotides. In various aspects, the oligonucleotides of the population have a size of at least 5, 6, 7, 8, 9, 10, 11, 12, 13, 14, 15, 16, 17, 18, 19, 20, 21, 22, 23, 24, 25, 26, 27, 28, 29, or 30 nucleotides. The size range may be an average size of the oligonucleotides in the population.

In some aspects, the oligonucleotides of the population have an average size of 7, 8, 9, 10, 11, 12, 13, 14, 15, 16, 17, 18, 19, 20, 21, 22, 23, 24, 25, 26, 27, 28, 29, or 30 nucleotides, wherein no more than 5, 6, 7, 8, 8, 9, 10, 11, 11, 12, 13, 14, 15, 15, 16, 17, 18, 19, 20, 20, 21, 22, 23, or 24, respectively, of the phosphate backbone linkages in each oligonucleotide is a p-ethoxy backbone linkage. In some aspects, the oligonucleotides of the population have an average size of 7, 8, 9, 10, 11, 12, 13, 14, 15, 16, 17, 18, 19, 20, 21, 22, 23, 24, 25, 26, 27, 28, 29, or 30 nucleotides and at least 2, 2, 2, 2, 3, 3, 3, 3, 4, 4, 4, 4, 4, 5, 5, 5, 5, 5, 5, 6, 6, 6, 6, or 6, respectively, of the phosphate backbone linkages in each oligonucleotide is a phosphodiester backbone linkage.

In some aspects, the population of oligonucleotides comprises a single species of oligonucleotides. In other aspects, the population of oligonucleotides comprises at least two species of oligonucleotides. A single species of oligonucleotide may have the same nucleotide sequence but either have or lack p-ethoxy linkages in different places within the molecule. In some aspects, the population of oligonucleotides comprises antisense oligonucleotides, short interfering RNAs (siRNAs), microRNAs (miRNAs), or piwiRNAs (piRNAs).

In certain aspects, the oligonucleotides of the population inhibit the expression of at least one oncogenic protein, infectious agent protein, or self-antigen. In some aspects, the oligonucleotides of the population hybridize with at least one oncogenic oligonucleotide, infectious agent oligonucleotide, or self-antigen oligonucleotide.

In various aspects, the composition further comprises phospholipids. In some aspects, the phospholipids are uncharged or have a neutral charge at physiologic pH. In some aspects, the phospholipids are neutral phospholipids. In certain aspects, the neutral phospholipids are phosphatidylcholines. In certain aspects, the neutral phospholipids are dioleoylphosphatidyl choline. In some aspects, the phospholipids are essentially free of cholesterol.

In some aspects, the phospholipids and oligonucleotides are present at a molar ratio of from about 5:1 to about 100:1, or any ratio derivable therein. In various aspects, the phospholipids and oligonucleotides are present at a molar ratio of about 5:1, 10:1, 15:1, 20:1, 25:1, 30:1, 35:1, 40:1, 45:1, 50:1, 55:1, 60:1, 65:1, 70:1, 75:1, 80:1, 85:1, 90:1 95:1, or 100:1. In some aspects, the oligonucleotides and phospholipids form an oligonucleotide-lipid complex, such as, for example, a liposome complex. In some aspects, at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% of the liposomes are less than 5 microns in diameter. In various aspects, the composition further comprises at least one surfactant, such as, for example, polysorbate 20. In some aspects, at least about 5% of the total liposomal p-Ethoxy antisense drug product consists of surfactant and at least about 90% of the liposomes are less than 5 microns in diameter. In some aspects, at least about 15% of the total liposomal p-Ethoxy antisense drug product consists of surfactant and at least about 90% of the liposomes are less than 3 microns in diameter. In some aspects, the population of oligonucleotides are incorporated in the population of liposomes.

In one aspect, the oligonucleotides of a population each comprise about 21 nucleotides in length and have about 30% phosphodiester backbone linkages. In one aspect, the population of oligonucleotides maybe further incorporated into a liposome composition comprising at least about 5% surfactant, wherein at least about 90% of said liposomes have a diameter of less than about 5 microns.

In one embodiment, pharmaceutical compositions are provided comprising a composition of oligonucleotides and phospholipids of the present embodiments and a pharmaceutically acceptable carrier. In some aspects, the composition further comprises a chemotherapeutic agent.

In one embodiment, methods are provided for delivering a therapeutically effective amount of an oligonucleotide to a cell comprising contacting the cell with a pharmaceutical composition of the present embodiments. In some aspects, the method is a method of treating hyperplasia, cancer, an autoimmune disease, or an infectious disease.

In one embodiment, methods are provided for treating a subject with cancer, an autoimmune disease, or an infectious disease comprising administering to the subject a therapeutically effective amount of a pharmaceutical composition of the present embodiments. In some aspects, the subject is a human. In some aspects, the cancer is a bladder, blood, pancreas, bone, bone marrow, brain, breast, colon, esophagus, stomach, head and neck, kidney, liver, lung, prostate, skin, testis, tongue, ovary, or uterine cancer. In some aspects, the autoimmune disease is Lupus erythematosis, Sjogren's disease, Crohn's disease, diabetes mellitus, multiple sclerosis, or rheumatoid arthritis. In some aspects, the infectious disease is a bacterial infection, fungal infection, viral infection, or parasitic infection. In some aspects, the composition is administered subcutaneously, intravenously, or intraperitoneally. In some aspects, the method further comprises administering at least a second anticancer therapy to the subject. In some aspects, the second anticancer therapy is a surgical therapy, chemotherapy, radiation therapy, cryotherapy, hormone therapy, immunotherapy, or cytokine therapy.

An oligonucleotide includes an antisense nucleic acid molecule that specifically hybridizes to a nucleic acid molecule encoding a target protein or regulating the expression of the target protein. "Specific hybridization" means that the antisense nucleic acid molecule hybridizes to the targeted nucleic acid molecule and regulates its expression. Preferably, "specific hybridization" also means that no other genes or transcripts are affected. An oligonucleotide can be a single-stranded nucleic acid and may comprise 7, 8, 9, 10, 11, 12, 13, 14, 15, 16, 17, 18, 19, 20, 21, 22, 23, 24, 25, 26, 27, 28, 29, 30 or more nucleobases. In particular aspects the oligonucleotide can comprise 15 to 30, 19 to 25, 20 to 23, or 21 contiguous nucleobases. In certain embodiments, the oligonucleotide inhibits the translation of a gene that promotes growth of a cancerous or pre-cancerous or hyperplastic mammalian cell (e.g., a human cell). An oligonucleotide may induce apoptosis in the cell, and/or inhibit the translation of an oncogene or other target gene. In certain embodiments, the oligonucleotide component comprises a single species of oligonucleotide. In other embodiments, the oligonucleotide component comprises a 2, 3, 4 or more species of oligonucleotide that target 1, 2, 3, 4, or more genes. The composition may further comprise a chemotherapeutic or other anti-cancer agent, which may or may not be incorporated in a lipid component or liposome of the invention. In further embodiments, the oligonucleotide component is incorporated within the liposome or lipid component.

"Entrap," "encapsulate," and "incorporate" refer to the lipid or liposome forming an impediment to free diffusion into solution by an association with or around an agent of interest, e.g., a liposome may encapsulate an agent within a lipid layer or within an aqueous compartment inside or between lipid layers. In certain embodiments, the composition is comprised in a pharmaceutically acceptable carrier. The pharmaceutically acceptable carrier may be formulated for administration to a human subject or patient.

In certain embodiments, the lipid component has an essentially neutral charge because it comprises a neutral phospholipid or a net neutral charge. In certain aspects a neutral phospholipid may be a phosphatidylcholine, such as DOPC, egg phosphatidylcholine ("EPC"), dilauryloylphosphatidylcholine ("DLPC"), dimyristoylphosphatidylcholine ("DMPC"), dipalmitoylphosphatidylcholine ("DPPC"), distearoylphosphatidylcholine ("DSPC"), 1-myristoyl-2- palmitoyl phosphatidylcholine ("MPPC"), 1-palmitoyl-2-myristoyl phosphatidylcholine ("PMPC"), 1-palmitoyl-2-stearoyl phosphatidylcholine ("PSPC"), 1-stearoyl-2-palmitoyl phosphatidylcholine ("SPPC"), dimyristyl phosphatidylcholine ("DMPC"), 1,2-distearoyl-sn-glycero-3-phosphocholine ("DAPC"), 1,2-diarachidoyl-sn-glycero-3-phosphocholine ("DBPC"), 1,2-dieicosenoyl-sn-glycero-3-phosphocholine ("DEPC"), palmitoyloeoyl phosphatidylcholine ("POPC"), lysophosphatidylcholine, or dilinoleoylphosphatidylcholine. In other aspects the neutral phospholipid can be a phosphatidylethanolamine, such as dioleoylphosphatidylethanolamine ("DOPE"), di stearoyl-phophatidyl ethanolamine ("DSPE"), dimyristoyl phosphatidylethanolamine ("DMPE"), dipalmitoyl phosphatidylethanolamine ("DPPE"), palmitoyloeoyl phosphatidylethanolamine ("POPE"), or lysophosphatidylethanol amine. In certain embodiments, the phospholipid component can comprise 1, 2, 3, 4, 5, 6, 7, 8, or more kinds or types of neutral phospholipid. In other embodiments, a phospholipid component can comprise 2, 3, 4, 5, 6 or more kinds or type of neutral phospholipids.

In certain embodiments, a lipid component can have an essentially neutral charge because it comprises a positively charged lipid and a negatively charged lipid. The lipid component may further comprise a neutrally charged lipid(s) or phospholipid(s). The positively charged lipid may be a positively charged phospholipid. The negatively charged lipid may be a negatively charged phospholipid. The negatively charged phospholipid may be a phosphatidylserine, such as dimyristoyl phosphatidylserine ("DMPS"), dipalmitoyl phosphatidylserine ("DPPS"), or brain phosphatidylserine ("BPS"). The negatively charged phospholipid may be a phosphatidylglycerol, such as dilauryloylphosphati dylglycerol ("DLPG"), dimyri stoylphosphatidylglycerol ("DMPG"), dipalmitoylphosphati dylglycerol ("DPPG"), distearoylphosphatidylglycerol ("DSPG"), or dioleoylphosphatidylglycerol ("DOPG"). In certain embodiments, the composition further comprises cholesterol or polyethyleneglycol (PEG). In other embodiments, the composition is essentially free of cholesterol. In certain embodiments, a phospholipid is a naturally-occurring phospholipid. In other embodiments, a phospholipid is a synthetic phospholipid.

Liposomes can be made of one or more phospholipids, as long as the lipid material is substantially uncharged. It is important that the composition be substantially free of anionic and cationic phospholipids and cholesterol. Suitable phospholipids include phosphatidyl cholines and others that are well known to persons that are skilled in this field.

Another aspect of the present invention involves methods for delivering oligonucleotide to a cell comprising contacting the cell with a neutral lipid composition of the invention. The methods will provide an inventive composition in an effective amount. An effective amount is an amount of therapeutic component that attenuates, slows, reduces or eliminates a cell, condition, or disease state in a subject. The cell may be comprised in a subject or patient, such as a human. The method may further comprise a method of treating cancer or other hyperplastic condition. The cancer may have originated in the bladder, blood, bone, bone marrow, brain, breast, colon, esophagus, gastrointestine, gum, head, kidney, liver, lung, nasopharynx, neck, prostate, skin, stomach, testis, tongue, or uterus. In certain embodiments, the method further comprises a method of treating a non-cancerous disease or hyperplastic condition. The cell may be a pre-cancerous or a cancerous cell. In certain embodiments, the compositions and methods inhibit the growth of the cell, induce apoptosis in the cell, and/or inhibit the translation of an oncogene. The oligonucleotide may inhibit the translation of a gene that is overexpressed in the cancerous cell.

In certain embodiments, the methods of the invention further comprise administering an additional therapy to the subject. The additional therapy may comprise administering a chemotherapeutic (e.g., paclitaxel or docetaxel), a surgery, a radiation therapy, and/or a gene therapy. In certain aspects the chemotherapy is docetaxel, paclitaxel, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein tansferase inhibitors, transplatinum, 5-fluorouracil, vincristin, vinblastin, methotrexate, or combinations thereof. In certain embodiments the chemotherapy is a taxane such as docetaxal or paclitaxel. The chemotherapy can be delivered before, during, after, or combinations thereof relative to a neutral lipid composition of the invention. A chemotherapy can be delivered within 0, 1, 5, 10, 12, 20, 24, 30, 48, or 72 hours or more of the neutral lipid composition. The neutral lipid composition, the second anti-cancer therapy, or both the neutral lipid composition and the anti-cancer therapy can be administered intratumorally, intravenously, intraperitoneally, subcutaneously, orally or by various combinations thereof.

It is contemplated that any embodiment discussed in this specification can be implemented with respect to any method or composition of the invention, and vice versa. Furthermore, compositions of the invention can be used to achieve the methods of the invention.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DESCRIPTION OF ILLUSTRATIVE EMBODIMENTS

The present invention provides compositions and methods for delivery of an oligonucleotide (e.g., an inhibitor of gene expression) to a cell via a lipid composition, in certain aspects a lipid composition with a net charge of about zero, i.e., a neutral lipid composition. In certain embodiments the lipid composition is a non-charged liposome. These methods may be effectively used to treat a cancer.

I. LIPIDS AND LIPOSOMES

"Liposomes" is used herein to mean lipid-containing vesicles having a lipid bilayer, as well as other lipid carrier particles that can entrap or incorporate antisense oligonucleotides. As such, liposome is a generic term encompassing a variety of unilamellar, multilamellar, and multivesicular lipid vehicles formed by the generation of enclosed lipid bilayers or aggregates. In addition, liposomes may have an undefined lamellar structure. Liposomes may be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). However, the present invention also encompasses compositions that have different structures in solution than the normal vesicular structure. For example, the lipids may assume a micellar structure or merely exist as non-uniform aggregates of lipid molecules.

Liposomes are a form of nanoparticles that are carriers for delivering a variety of drugs into a diseased tissue. Optimal liposome size depends on the target tissue. In tumor tissue, the vasculature is discontinuous, and pore sizes vary from 100 to 780 nm (Siwak et al., 2002). By comparison, pore size in normal vascular endothelium is <2 nm in most tissues, and 6 nm in post-capillary venules. Negatively charged liposomes are thought to be more rapidly removed from circulation than neutral or positively charged liposomes; however, recent studies have indicated that the type of negatively charged lipid affects the rate of liposome uptake by the reticulo-endothelial system (RES). For example, liposomes containing negatively charged lipids that are not sterically shielded (phosphatidylserine, phosphatidic acid, and phosphatidylglycerol) are cleared more rapidly than neutral liposomes. Interestingly, cationic liposomes (1,2-dioleoyl-3-trimethylammonium-propane [DOTAP]) and cationic-liposome-DNA complexes are more avidly bound and internalized by endothelial cells of angiogenic blood vessels via endocytosis than anionic, neutral, or sterically stabilized neutral liposomes (Thurston et al., 1998; Krasnici et al., 2003). Cationic liposomes may not be ideal delivery vehicles for tumor cells because surface interactions with the tumor cells create an electrostatically derived binding-site barrier effect, inhibiting further association of the delivery systems with tumor spheroids (Kostarelos et al., 2004). However, neutral liposomes appear to have better intratumoral penetration. Toxicity with specific liposomal preparations has also been a concern. Cationic liposomes elicit dose-dependent toxicity and pulmonary inflammation by promoting release of reactive oxygen intermediates, and this effect is more pronounced with multivalent cationic liposomes than monovalent cationic liposomes, such as DOTAP (Dokka et al., 2000). Neutral and negative liposomes do not appear to exhibit lung toxicity (Guitierrez-Puente et al., 1999). Cationic liposomes, while efficiently taking up nucleic acids, have had limited success for in vivo gene down-regulation, perhaps because of their stable intracellular nature and resultant failure to release nucleic acid contents. Lipids with neutral charge or lipid compositions with a neutralized charge, e.g., 1,2-dioleoyl-sn-glycero-3-phosphocholine (DOPC), are used herein because of the neutral properties and success in delivering antisense oligonucleotides in vivo.

The present invention provides methods and compositions for associating an oligonucleotide, such as an antisense oligonucleotide, with a lipid and/or liposome. The oligonucleotide may be incorporated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. The liposome or liposome/oligonucleotide-associated compositions provided herein are not limited to any particular structure in solution. For example, they may be present in a bilayer structure, as micelles, or with a "collapsed" structure. They may also simply be interspersed in a solution, possibly forming aggregates that are not uniform in either size or shape.

A. Lipids

Lipids are fatty substances that may be naturally occurring or synthetic. For example, lipids include the fatty droplets that naturally occur in the cytoplasm as well as the class of compounds that are well known to those of skill in the art that contain long-chain aliphatic hydrocarbons and their derivatives, such as fatty acids, alcohols, amines, amino alcohols, and aldehydes. An example is the lipid 1,2-dioleoyl-sn-glycero-3-phosphocholine (DOPC).

Lipid compositions of the present invention may comprise phospholipids. In certain embodiments, a single kind or type of phospholipid may be used in the creation of lipid compositions, such as liposomes. In other embodiments, more than one kind or type of phospholipid may be used.

Phospholipids include glycerophospholipids and certain sphingolipids. Phospholipids include, but are not limited to, dioleoylphosphatidylycholine ("DOPC"), egg phosphatidylcholine ("EPC"), dilauryloylphosphatidylcholine ("DLPC"), dimyristoylphosphatidylcholine ("DMPC"), dipalmitoylphosphatidylcholine ("DPPC"), distearoylphosphatidylcholine ("DSPC"), 1-myristoyl-2-palmitoyl phosphatidylcholine ("MPPC"), 1-palmitoyl-2-myristoyl phosphatidylcholine ("PMPC"), 1-palmitoyl-2-stearoyl phosphatidylcholine ("PSPC"), 1-stearoyl-2-palmitoyl phosphatidylcholine ("SPPC"), dilauryloylphosphatidylglycerol ("DLPG"), dimyristoylphosphatidylglycerol ("DMPG"), dipalmitoylphosphatidylglycerol ("DPPG"), distearoylphosphatidylglycerol ("DSPG"), distearoyl sphingomyelin ("DSSP"), distearoylphophatidyl ethanolamine ("DSPE"), dioleoylphosphatidylglycerol ("DOPG"), dimyristoyl phosphatidic acid ("DMPA"), dipalmitoyl phosphatidic acid ("DPPA"), dimyristoyl phosphatidylethanolamine ("DMPE"), dipalmitoyl phosphatidylethanolamine ("DPPE"), dimyristoyl phosphatidylserine ("DMPS"), dipalmitoyl phosphatidylserine ("DPPS"), brain phosphatidylserine ("BPS"), brain sphingomyelin ("BSP"), dipalmitoyl sphingomyelin ("DPSP"), dimyristyl phosphatidylcholine ("DMPC"), 1,2-distearoyl-sn-glycero-3- phosphocholine ("DAPC"), 1,2-diarachidoyl-sn-glycero-3-phosphocholine ("DBPC"), 1,2-dieicosenoyl-sn-glycero-3-phosphocholine ("DEPC"), dioleoylphosphatidyl ethanolamine ("DOPE"), palmitoyloeoyl phosphatidylcholine ("POPC"), palmitoyloeoyl phosphatidyletlianolamine ("POPE"), lysophosphatidylcholine, lysophosphatidylethanolamine, and dilinoleoylphosphatidylcholine.

Phospholipids include, for example, phosphatidylcholines, phosphatidylglycerols, and phosphatidylethanolamines; because phosphatidylethanolamines and phosphatidylcholines are non-charged under physiological conditions (i.e., at about pH 7), these compounds may be particularly useful for generating neutral liposomes. In certain embodiments, the phospholipid DOPC is used to produce non-charged liposomes or lipid compositions. In certain embodiments, a lipid that is not a phospholipid (e.g., a cholesterol) can also be used Phospholipids may be from natural or synthetic sources. However, phospholipids from natural sources, such as egg or soybean phosphatidylcholine, brain phosphatidic acid, brain or plant phosphatidylinositol, heart cardiolipin, and plant or bacterial phosphatidylethanolamine, are not used in certain embodiments as the primary phosphatide (i.e., constituting 50% or more of the total phosphatide composition) because this may result in instability and leakiness of the resulting liposomes.

B. Neutral Liposomes

"Neutral liposomes or lipid composition" or "non-charged liposomes or lipid composition," as used herein, are defined as liposomes or lipid compositions having one or more lipids that yield an essentially-neutral net charge (substantially non-charged). In certain embodiments, neutral liposomes or lipid compositions may include mostly lipids and/or phospholipids that are themselves neutral. In certain embodiments, amphipathic lipids may be incorporated into or used to generate neutral liposomes or lipid compositions. For example, a neutral liposome may be generated by combining positively and negatively charged lipids so that those charges substantially cancel one another, thereby yielding an essentially-neutral net charge. By "essentially neutral" or "essentially non-charged," it is meant that few, if any, lipids within a given population (e.g., a population of liposomes) include a charge that is not canceled by an opposite charge of another component (e.g., fewer than 10% of components include a non-canceled charge, more preferably fewer than 5%, and most preferably fewer than 1%). In certain embodiments of the present invention, a composition may be prepared wherein the lipid component of the composition is essentially neutral but is not in the form of liposomes.

The size of the liposomes varies depending on the method of synthesis. A liposome suspended in an aqueous solution is generally in the shape of a spherical vesicle, and may have one or more concentric layers of lipid bilayer molecules. Each layer consists of a parallel array of molecules represented by the formula XY, wherein X is a hydrophilic moiety and Y is a hydrophobic moiety. In aqueous suspension, the concentric layers are arranged such that the hydrophilic moieties tend to remain in contact with an aqueous phase and the hydrophobic regions tend to self-associate. For example, when aqueous phases are present both within and without the liposome, the lipid molecules may form a bilayer, known as a lamella, of the arrangement XY-YX. Aggregates of lipids may form when the hydrophilic and hydrophobic parts of more than one lipid molecule become associated with each other. The size and shape of these aggregates will depend upon many different variables, such as the nature of the solvent and the presence of other compounds in the solution.

Liposomes within the scope of the present invention can be prepared in accordance with known laboratory techniques, such as, for example, the method of Bangham et al. (1965), the contents of which are incorporated herein by reference; the method of Gregoriadis (1979), the contents of which are incorporated herein by reference; the method of Deamer and Uster (1983), the contents of which are incorporated by reference; and the reverse-phase evaporation method as described by Szoka and Papahadjopoulos (1978). The aforementioned methods differ in their respective abilities to entrap aqueous material and their respective aqueous space-to-lipid ratios.

In certain embodiments, a neutral liposome may be used to deliver an oligonucleotide, such as an antisense oligonucleotide. The neutral liposome may contain a single species of oligonucleotide directed to the suppression of translation of a single gene, or the neutral liposome may contain multiple species of oligonucleotides that are directed to the suppression of translation of multiple genes. Further, the neutral liposome may also contain a chemotherapeutic in addition to the oligonucleotide; thus, in certain embodiments, a chemotherapeutic and an oligonucleotide may be delivered to a cell (e.g., a cancerous cell in a human subject) in the same or separate compositions.

Dried lipids or lyophilized liposomes may be dehydrated and reconstituted at an appropriate concentration with a suitable solvent (e.g., DPBS or Hepes buffer). The mixture may then be vigorously shaken in a vortex mixer. The liposomes may be resuspended at an appropriate total phospholipid concentration (e.g., about 10-200 mM). Unencapsulated oligonucleotide may be removed by centrifugation at 29,000 g and the liposomal pellets washed. Alternatively, the unencapsulated oligonucleotides may be removed by dialyzing against an excess of solvent. The amount of oligonucleotide encapsulated can be determined in accordance with standard methods.

II. INHIBITION OF GENE EXPRESSION

An inhibitory oligonucleotide can inhibit the transcription or translation of a gene in a cell. An oligonucleotide may be from 5 to 50 or more nucleotides long, and in certain embodiments from 7 to 30 nucleotides long. In certain embodiments, the oligonucleotide maybe 7, 8, 9, 10, 11, 12, 13, 14, 15, 16, 17, 18, 19, 20, 21, 22, 23, 24, 25, 26, 27, 28, 29, or 30 nucleotides long. The oligonucleotide may comprise a nucleic acid and/or a nucleic acid analog. Typically, an inhibitory oligonucleotide will inhibit the translation of a single gene within a cell; however, in certain embodiments, an inhibitory oligonucleotide may inhibit the translation of more than one gene within a cell.

Within an oligonucleotide, the components of the oligonucleotide need not be of the same type or homogenous throughout (e.g., an oligonucleotide may comprise a nucleotide and a nucleic acid or nucleotide analog). In certain embodiments of the present invention, the oligonucleotide may comprise only a single nucleic acid or nucleic acid analog. The inhibitory oligonucleotide may comprise 5, 6, 7, 8, 9, 10, 11, 12, 13, 14, 15, 16, 17, 18, 19, 20, 25, 30 or more contiguous nucleobases, including all ranges therebetween, that hybridize with a complementary nucleic acid to form a double-stranded structure.

III. NUCLEIC ACIDS

The present invention provides methods and compositions for the delivery of an oligonucleotide via neutral liposomes. Because an oligonucleotide is composed of a nucleic acid, methods relating to nucleic acids (e.g., production of a nucleic acid, modification of a nucleic acid, etc.) may also be used with regard to an oligonucleotide.

The term "nucleic acid" is well known in the art. A "nucleic acid" as used herein generally refers to a molecule (i.e., a strand) of DNA, RNA, or a derivative or analog thereof, comprising a nucleobase. These definitions refer to a single-stranded or double-stranded nucleic acid. Double-stranded nucleic acids may be formed by fully complementary binding; however, in some embodiments, a double-stranded nucleic acid may be formed by partial or substantial complementary binding. As used herein, a single-stranded nucleic acid may be denoted by the prefix "ss" and a double-stranded nucleic acid by the prefix "ds."

A. Nucleobases

As used herein a "nucleobase" refers to a heterocyclic base, such as, for example, a naturally occurring nucleobase (i.e., an A, T, G, C or U) found in at least one naturally occurring nucleic acid (i.e., DNA and RNA), and naturally or non-naturally occurring derivative(s) and analogs of such a nucleobase. A nucleobase generally can form one or more hydrogen bonds (i.e., "anneal" or "hybridize") with at least one naturally occurring nucleobase in a manner that may substitute for naturally occurring nucleobase pairing (e.g., the hydrogen bonding between A and T, G and C, and A and U). A nucleobase may be comprised in a nucleoside or nucleotide, using any chemical or natural synthesis method described herein or known to one of ordinary skill in the art.

"Purine" and/or "pyrimidine" nucleobase(s) encompass naturally occurring purine and/or pyrimidine nucleobases and also derivative(s) and analog(s) thereof, including but not limited to, a purine or pyrimidine substituted by one or more of an alkyl, carboxyalkyl, amino, hydroxyl, halogen (i.e., fluoro, chloro, bromo, or iodo), thiol, or alkylthiol moiety. Preferred alkyl (e.g., alkyl, caboxyalkyl, etc.) moieties comprise of from about 1, about 2, about 3, about 4, about 5, to about 6 carbon atoms. Other non-limiting examples of a purine or pyrimidine include a deazapurine, a 2,6-diaminopurine, a 5-fluorouracil, a xanthine, a hypoxanthine, a 8-bromoguanine, a 8-chloroguanine, a bromothyline, a 8-aminoguanine, a 8-hydroxyguanine, a 8-methylguanine, a 8-thioguanine, an azaguanine, a 2-aminopurine, a 5-ethylcytosine, a 5-methylcyosine, a 5-bromouracil, a 5-ethyluracil, a 5-iodouracil, a 5-chlorouracil, a 5-propyluracil, a thiouracil, a 2-methyladenine, a methylthioadenine, a N,N-diemethyladenine, an azaadenines, a 8-bromoadenine, a 8-hydroxyadenine, a 6-hydroxyaminopurine, a 6-thiopurine, a 4-(6-aminohexyl/cytosine), and the like. Purine and pyrimidine derivatives or analogs include, but are not limited to (abbreviation/modified base description): ac4c/4-acetylcytidine, Mam5s2u/5-methoxyaminomethyl-2-thiouridine, Chm5u/5-(carboxyhydroxylmethyl) uridine, Man q/Beta, D-mannosylqueosine, Cm/2'-O-methylcytidine, Mcm5s2u/5-methoxycarbonylmethyl-2-thiouridine, Cmnm5 s2u/5-carboxymethylamino-methyl-2-thioridine, Mcm5u/5-methoxycarbonylmethyluridine, Cmnm5u/5-carboxymethyl aminomethyluridine, Mo5u/5-methoxyuridine, D/Dihydrouridine, Ms2i6a, 2-methylthio-N6-isopentenyladenosine, Fm/2'-O-methylpseudouridine, Ms2t6a/N-((9-beta-D-ribofuranosyl-2-methylthiopurine-6-yl)carb amoyl)threonine, Gal q/Beta,D-galactosylqueosine, Mt6a/N-((9-beta-D-ribofuranosylpurine-6-yl)N-methyl-carbamoyl)threonine, Gm/2'-O-methylguanosine, Mv/Uridine-5-oxyacetic acid methylester, I/Inosine, o5u/Uridine-5-oxyacetic acid (v), I6a/N6-isopentenyladenosine, Osyw/Wybutoxosine, m1a/1-methyladenosine, P/Pseudouridine, m1f/1-methylpseudouridine, Q/Queosine, m1g/1-methylguanosine, s2c/2-thiocytidine, m1I/1-methylinosine, s2t/5-methyl-2-thiouridine, m22g/2,2-dimethylguanosine, s2u/2-thiouridine, m2a/2-methyladenosine, s4u/4-thiouridine, m2g/2-methylguanosine, T/5-methyluridine, m3c/3-methylcytidine, t6a/N-((9-b eta-D-ribofuranosylpurine-6-yl)carbamoyl)threonine, m5c/5-methylcytidine, Tm/2'-O-methyl-5-methyluridine, m6a/N6-methyladenosine, Um/2'-O-methyluridine, m7g/7-methylguanosine, Yw/Wybutosine, Mam5u/5-methylaminomethyluridine, or X/3-(3-amino-3-carboxypropyl)uridine, (acp3)u.

B. Nucleosides

As used herein, a "nucleoside" refers to an individual chemical unit comprising a nucleobase covalently attached to a nucleobase linker moiety. A non-limiting example of a "nucleobase linker moiety" is a sugar comprising 5-carbon atoms (i.e., a "5-carbon sugar"), including but not limited to a deoxyribose, a ribose, an arabinose, or a derivative or an analog of a 5-carbon sugar. Non-limiting examples of a derivative or an analog of a 5-carbon sugar include a 2'-fluoro-2'-deoxyribose or a carbocyclic sugar where a carbon is substituted for an oxygen atom, in the sugar ring. As used herein, a "moiety" generally refers to a smaller chemical or molecular component of a larger chemical or molecular structure.

Different types of covalent attachment(s) of a nucleobase to a nucleobase linker moiety are known in the art. By way of non-limiting example, a nucleoside comprising a purine (i.e., A or G) or a 7-deazapurine nucleobase typically comprises a covalent attachment of the 9 position of the purine or 7-deazapurine to a 1'-position of a 5-carbon sugar. In another non-limiting example, a nucleoside comprising a pyrimidine nucleobase (i.e., C, T, or U) typically comprises a covalent attachment of the 1 position of the pyrimidine to a 1'-position of a 5-carbon sugar (Kornberg and Baker, 1992).

C. Nucleotides

As used herein, a "nucleotide" refers to a nucleoside further comprising a "backbone linkage." A backbone linkage generally covalently attaches a nucleotide to another molecule comprising a nucleotide, or to another nucleotide to form a nucleic acid. The "backbone linkage" in naturally occurring nucleotides typically comprises a phosphate moiety (e.g., a phosphodiester backbone linkage), which is covalently attached to a 5-carbon sugar. The attachment of the backbone moiety typically occurs at either the 3'- or 5'-position of the 5-carbon sugar. However, other types of attachments are known in the art, particularly when a nucleotide comprises derivatives or analogs of a naturally occurring 5-carbon sugar or phosphate moiety.

D. Nucleic Acid Analogs

A nucleic acid may comprise, or be composed entirely of, a derivative or analog of a nucleobase, a nucleobase linker moiety, and/or backbone linkage that may be present in a naturally occurring nucleic acid. As used herein a "derivative" refers to a chemically modified or altered form of a naturally occurring molecule, while the terms "mimic" or "analog" refer to a molecule that may or may not structurally resemble a naturally occurring molecule or moiety, but possesses similar functions. Nucleobase, nucleoside, and nucleotide analogs or derivatives are well known in the art.

Non-limiting examples of nucleosides, nucleotides, or nucleic acids comprising 5-carbon sugar and/or backbone linkage derivatives or analogs, include those in U.S. Pat. No. 5,681,947 which describes oligonucleotides comprising purine derivatives that form triple helixes with and/or prevent expression of dsDNA; U.S. Pat. Nos. 5,652,099 and 5,763,167 which describe nucleic acids incorporating fluorescent analogs of nucleosides found in DNA or RNA, particularly for use as fluorescent nucleic acids probes; U.S. Pat. No. 5,614,617 which describes oligonucleotide analogs with substitutions on pyrimidine rings that possess enhanced nuclease stability; U.S. Pat. Nos. 5,670,663, 5,872,232 and 5,859,221 which describe oligonucleotide analogs with modified 5-carbon sugars (i.e., modified 2'-deoxyfuranosyl moieties) used in nucleic acid detection; U.S. Pat. No. 5,446,137 which describes oligonucleotides comprising at least one 5-carbon sugar moiety substituted at the 4' position with a substituent other than hydrogen that can be used in hybridization assays; U.S. Pat. No. 5,886,165 which describes oligonucleotides with both deoxyribonucleotides with 3'-5' backbone linkages and ribonucleotides with 2'-5' backbone linkages; U.S. Pat. No. 5,714,606 which describes a modified backbone linkage wherein a 3'-position oxygen of the backbone linkage is replaced by a carbon to enhance the nuclease resistance of nucleic acids; U.S. Pat. No. 5,672,697 which describes oligonucleotides containing one or more 5' methylene phosphonate backbone linkages that enhance nuclease resistance; U.S. Pat. Nos. 5,466,786 and 5,792,847 which describe the linkage of a substituent moiety that may comprise a drug or label to the 2' carbon of an oligonucleotide to provide enhanced nuclease stability and ability to deliver drugs or detection moieties; U.S. Pat. No. 5,223,618 which describes oligonucleotide analogs with a 2 or 3 carbon backbone linkage attaching the 4' position and 3' position of adjacent 5-carbon sugar moiety to enhanced cellular uptake, resistance to nucleases, and hybridization to target RNA; U.S. Pat. No. 5,470,967 which describes oligonucleotides comprising at least one sulfamate or sulfamide backbone linkage that are useful as nucleic acid hybridization probes; U.S. Pat. Nos. 5,378,825, 5,777,092, 5,623,070, 5,610,289 and 5,602,240 which describe oligonucleotides with a three or four atom backbone linkage moiety replacing the phosphodiester backbone linkage used for improved nuclease resistance, cellular uptake, and regulating RNA expression; U.S. Pat. No. 5,858,988 which describes hydrophobic carrier agent attached to the 2'-O position of oligonucleotides to enhance their membrane permeability and stability; U.S. Pat. No. 5,214,136 which describes oligonucleotides conjugated to anthraquinone at the 5' terminus that possess enhanced hybridization to DNA or RNA; enhanced stability to nucleases; U.S. Pat. No. 5,700,922 which describes PNA-DNA-PNA chimeras wherein the DNA comprises 2'-deoxy-erythro-pentofaranosyl nucleotides for enhanced nuclease resistance, binding affinity, and ability to activate RNase H; U.S. Pat. No. 5,708,154 which describes RNA linked to a DNA to form a DNA-RNA hybrid; U.S. Pat. No. 5,908,845 which describes polyether nucleic acids wherein one or more nucleobases are linked to chiral carbon atoms in a polyether backbone; U.S. Pat. Nos. 5,786,461, 5,891,625, 5,786,461, 5,773,571, 5,766,855, 5,736,336, 5,719,262, 5,714,331, 5,539,082, and WO 92/20702 which describe peptide nucleic acids (PNA or peptide-based nucleic acid analog; or PENAM) that generally comprise one or more nucleotides or nucleosides that comprise a nucleobase moiety, a nucleobase linker moiety that is not a 5-carbon sugar (e.g., aza nitrogen atoms, amido and/or ureido tethers), and/or a backbone linkage that is not a phosphate backbone linkage (e.g., aminoethylglycine, polyamide, polyethyl, polythioamide, polysulfinamide, or polysulfonamide backbone linkage); and U.S. Pat. No. 5,855,911 which describes the hydrophobic, nuclease resistant p-ethoxy backbone linkage.

Other modifications and uses of nucleic acid analogs are known in the art, and it is anticipated that these techniques and types of nucleic acid analogs may be used with the present invention.

E. Preparation of Nucleic Acids

A nucleic acid may be made by any technique known to one of ordinary skill in the art, such as chemical synthesis, enzymatic production or biological production. Non-limiting examples of a synthetic nucleic acid (e.g., a synthetic oligonucleotide) include a nucleic acid made by in vitro chemical synthesis using phosphotriester, phosphite, or phosphoramidite chemistry and solid phase techniques, such as described in EP 266,032, incorporated herein by reference, or by deoxynucleoside H-phosphonate intermediates as described by Froehler et al. (1986) and U.S. Pat. No. 5,705,629, each incorporated herein by reference. In the methods of the present invention, one or more species of oligonucleotide may be used. Various mechanisms of oligonucleotide synthesis have been disclosed in, for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

F. Purification of Nucleic Acids

A nucleic acid may be purified on polyacrylamide gels, cesium chloride centrifugation gradients, or by any other means known to one of ordinary skill in the art (see for example, Sambrook et al. (2001), incorporated herein by reference).

In certain embodiments, the present invention concerns a nucleic acid that is an isolated nucleic acid. As used herein, the term "isolated nucleic acid" refers to a nucleic acid molecule (e.g., an RNA or DNA molecule) that has been isolated free of, or is otherwise free of, the bulk of the total genomic and transcribed nucleic acids of one or more cells. In certain embodiments, "isolated nucleic acid" refers to a nucleic acid that has been isolated free of, or is otherwise free of, the bulk of cellular components or in vitro reaction components, such as, for example, macromolecules, such as lipids or proteins, small biological molecules, and the like.

G. Hybridization

As used herein, "hybridization," "hybridize(s)," or "capable of hybridizing" is understood to mean the forming of a double or triple stranded molecule or a molecule with partial double or triple stranded nature. The term "anneal" as used herein is synonymous with "hybridize."

As used herein "stringent condition(s)" or "high stringency" are those conditions that allow hybridization between or within one or more nucleic acid strand(s) containing complementary sequence(s), but precludes hybridization of random sequences. Stringent conditions tolerate little, if any, mismatch between a nucleic acid and a target strand. Such conditions are well known to those of ordinary skill in the art, and are preferred for applications requiring high selectivity.

Stringent conditions may comprise low salt and/or high temperature conditions, such as provided by about 0.02 M to about 0.15 M NaCl at temperatures of about 50° C. to about 70° C. It is understood that the temperature and ionic strength of a desired stringency are determined in part by the length of the particular nucleic acid(s), the length and nucleobase content of the target sequence(s), the charge composition of the nucleic acid(s), and to the presence or concentration of formamide, tetramethylammonium chloride, or other solvent(s) in a hybridization mixture.

It is also understood that these ranges, compositions and conditions for hybridization are mentioned by way of non-limiting examples only, and that the desired stringency for a particular hybridization reaction is often determined empirically by comparison to one or more positive or negative controls. Depending on the application envisioned it is preferred to employ varying conditions of hybridization to achieve varying degrees of selectivity of a nucleic acid towards a target sequence. In a non-limiting example, identification or isolation of a related target nucleic acid that does not hybridize to a nucleic acid under stringent conditions may be achieved by hybridization at low temperature and/or high ionic strength. Such conditions are termed "low stringency" or "low stringency conditions," and non-limiting examples of low stringency include hybridization performed at about 0.15 M to about 0.9 M NaCl at a temperature range of about 20° C. to about 50° C. Of course, it is within the skill of one in the art to further modify the low or high stringency conditions to suite a particular application.

IV. METHODS OF MANUFACTURING LIPOSOMAL P-ETHOXY ANTISENSE DRUG PRODUCT

The liposomal p-ethoxy antisense drug product is composed of two cGMP products, both of which have a FDA-required Certificate of Analysis with FDA-approved release criteria. The raw materials, solvents, and final drug product are described herein. When manufactured, the drug product is a lyophilized crystal or powder of amber or white color that comprises the following materials: oligonucleotide (e.g., p-ethoxy antisense drug substance), neutral lipids (e.g., DOPC), and surfactant (e.g., polysorbate 20). In preparation for administration to a patient, normal saline is added to the vial, at which time liposomes are formed with the p-ethoxy antisense incorporated into the interior.

Specific physical properties (e.g., solubility and hydrophobicity, which then affect drug product solubility in saline, incorporation of oligo into liposomes, and liposome particle size) of the finished product can be defined using a predetermined p-ethoxy and phosphodiester amidite raw material mix during production of the p-ethoxy antisense drug substance. Increasing the number of p-ethoxy molecules in the backbone of the oligonucleotide causes the molecule to be more hydrophobic (which results in larger liposome particles), less polar, and less soluble. As the oligonucleotide becomes less soluble due to a greater number of p-ethoxy backbone linkages, the reconstituted solution becomes whiter until particulates form as hydrophobicity becomes too high.

The effect of the surfactant (polysorbate 20) on liposome particle size was determined by titrating the amount of surfactant. In the absence of polysorbate 20, only 2.8% of the particles had a diameter of 300 nm or less. In the presence of 1× polysorbate 20 (about 5% of the total liposomal p-ethoxy antisense drug product), 12.5% of the particles had a diameter of 300 nm or less. With the addition of 3×-10× polysorbate 20, around 20% of the particles had a diameter of 300 nm or less. Thus an increase in surfactant from 1× to 3× results in a decrease in particle size.

V. METHODS OF TESTING LIPOSOMAL P-ETHOXY ANTISENSE DRUG PRODUCT

Visual Inspection of Manufactured Drug Product:

After manufacturing, a sample vial containing drug product is selected and visually inspected. The absence of liquid is mandatory, and then amber crystals at the bottom of the vial are acceptable, and increasing in acceptance to a white, flocculated powder or appearance, the best result. The white appearance indicates a better drying process, with a high surface area to mass ratio, which is very conducive to reconstitution for use.

Visual Inspection of Reconstituted Drug Ready for Patient IV:

Normal saline is added to a vial containing the manufactured Liposomal P-ethoxy Antisense Drug Product and shaken to reconstitute into a solution with the drug crystal or powder completely dissolved. Three main observations are made: 1) that the crystal or powder is completely dissolved, 2) there are no white clumps of undissolved material, and 3) the appearance is a milky white or skim milk appearance. The bluer the appearance of the reconstituted liquid, the better, as this signals a smaller liposome particle size that reflects light in the blue spectrum.

Mass Spectrometry:

Mass spectrometry (mass spec) is used to display the profile of the various masses in a sample. When p-ethoxy antisense material is produced, a mass spec is run on the sample. The result shows peaks of material present on a grid that has increasing mass on the "x" axis to the right, and relative mass abundance on the "y" axis increasing upward. The profile from a sample is analyzed to determine the relative quantity of p-ethoxy backbones in the p-ethoxy sample, recognizing that the profile of peaks represents (starting farthest to the right), full length material with all backbones comprised of the p-ethoxy linkage, the next peak moving left a full length with one backbone with a p-ethoxy deletion (and therefore, the ethyl being knocked off and the result being a normal phosphodiester backbone linkage), and continuing. The mass spec pattern shifted to the right represents a p-ethoxy sample having more p-ethoxy backbones, and therefore having the properties of being more hydrophobic and less soluble; and likewise, shifted to the left having the opposite effects. Inspection of the mass spec chart of a sample also can be used to determine if filtration during manufacturing produces any adverse effects on oligonucleotide composition present in the filtered drug product.

UV Testing:

Ultraviolent light testing is used to determine the mass of oligonucleotide present in a sample. Oligonucleotides absorb light in the 260 nanometer range. As a result, UV testing of the finished reconstituted drug product has come to be used as a method in determining the quantity of oligonucleotide drug substance in a vial of drug product. In terms of manufacturing development and innovations, UV testing was used to determine if there were problems experienced during filtration in manufacturing or poor solubility of the p-ethoxy antisense drug substance, resulting in less oligonucleotide in solution and therefore a lower UV reading. The method will be validated and likely become part of the final product release testing.

Liposome Particle Size:

A vial of finished drug product is reconstituted and tested for liposome particle size. The result is often a roughly normal distribution, having a central point, tails and average values or a roughly normal distribution of the majority of the particles and smaller, secondary peaks of the smaller liposomes particles resulting from second-order particle formation effects. It is important that liposome particles not be too large, as they may create adverse effects in patients (for example, create blood flow problems in smaller blood vessels in the lungs). As a result, the drug product release criteria include that particle size testing show that 90% of liposomes be about 5 microns or less in size or about 3 micron or less in size. In addition, smaller liposomes are preferred because they will have better uptake into cells, and secondly, smaller liposomes can penetrate vascular pores, thereby allowing the liposomes to penetrate inside tumors, increasing treatment effectiveness of a Liposomal P-ethoxy Antisense Drug Product.

VI. METHODS OF TREATMENT

Certain aspects of the present invention provide an oligonucleotide-lipid complex (e.g., an oligonucleotide incorporated into a non-charged liposome) for treating diseases, such as cancer, autoimmune disease, or infectious disease. Particularly, the oligonucleotide may have a sequence that allows for base pairing with a human nucleotide sequence and thus may inhibit the expression of a protein encoded by the human nucleotide sequence.

"Treatment" and "treating" refer to administration or application of a therapeutic agent to a subject or performance of a procedure or modality on a subject for the purpose of obtaining a therapeutic benefit of a disease or health-related condition. For example, a treatment may include administration of a pharmaceutically effective amount of an oligonucleotide-lipid complex.

"Subject" and "patient" refer to either a human or non-human, such as primates, mammals, and vertebrates. In particular embodiments, the subject is a human.

The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease. For example, treatment of cancer may involve, for example, a reduction in the size of a tumor, a reduction in the invasiveness of a tumor, reduction in the growth rate of the cancer, or prevention of metastasis. Treatment of cancer may also refer to prolonging survival of a subject with cancer. Treatment of an autoimmune disease may involve, for example, reducing the expression of a self-antigen against which there is an undesired immune response, inducing tolerance of a self-antigen against which there is an undesired immune response, or inhibiting the immune response towards the self-antigen. Treatment of an infectious disease may involve, for example, eliminate the infectious agent, reduce the level of the infectious agent, or maintain the level of the infectious agent at a certain level.

Tumors for which the present treatment methods are useful include any malignant cell type, such as those found in a solid tumor, a hematological tumor, metastatic cancer, or non-metastatic cancer. Exemplary solid tumors can include, but are not limited to, a tumor of an organ selected from the group consisting of pancreas, colon, cecum, esophagus, gastrointestine, gum, liver, skin, stomach, testis, tongue, uterus, stomach, brain, head, neck, ovary, kidney, larynx, sarcoma, bone, lung, bladder, melanoma, prostate, and breast. Exemplary hematological tumors include tumors of the bone marrow, T or B cell malignancies, leukemias, lymphomas, blastomas, myelomas, and the like. Further examples of cancers that may be treated using the methods provided herein include, but are not limited to, carcinoma, lymphoma, blastoma, sarcoma, leukemia, squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer and gastrointestinal stromal cancer), pancreatic cancer, glioblastoma, cervical cancer, ovarian cancer, liver cancer, bladder cancer, breast cancer, colon cancer, colorectal cancer, endometrial or uterine carcinoma, salivary gland carcinoma, kidney or renal cancer, prostate cancer, vulval cancer, thyroid cancer, various types of head and neck cancer, melanoma, superficial spreading melanoma, lentigo malignant melanoma, acral lentiginous melanomas, nodular melanomas, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's macroglobulinemia), chronic lymphocytic leukemia (CLL), acute lymphoblastic leukemia (ALL), Hairy cell leukemia, multiple myeloma, acute myeloid leukemia (AML) and chronic myeloblastic leukemia.

The cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

Autoimmune diseases for which the present treatment methods are useful include, without limitation, spondyloarthropathy, ankylosing spondylitis, psoriatic arthritis, reactive arthritis, enteropathic arthritis, diabetes mellitus, celiac disease, autoimmune thyroid disease, autoimmune liver disease, Addison's disease, transplant rejection, graft vs. host disease, host vs. graft disease, ulcerative colitis, Crohn's disease, irritable bowel disease, inflammatory bowel disease, rheumatoid arthritis, juvenile rheumatoid arthritis, familial Mediterranean fever, amyotrophic lateral sclerosis, Sjogren's syndrome, early arthritis, viral arthritis, multiple sclerosis, or psoriasis. The diagnosis and treatment of these diseases are well documented in the literature.

Infectious diseases for which the present treatment methods are useful include, without limitation, bacterial infections, viral infections, fungal infections, and parasitic infections. Exemplary viral infections include hepatitis B virus, hepatitis C virus, human immunodeficiency virus 1, human immunodeficiency virus 2, human papilloma virus, herpes simplex virus 1, herpes simplex virus 2, herpes zoster, varicella zoster, coxsackievirus A16, cytomegalovirus, ebola virus, enterovirus, Epstein-Barr virus, hanta virus, hendra virus, viral meningitis, respiratory syncytial virus, rotavirus, west nile virus, adenovirus, and influenza virus infections. Exemplary bacterial infections include *Chlamydia trachomatis, Listeria monocytogenes, Helicobacter pylori, Escherichia coli, Borelia burgdorferi, Legionella pneumophilia, Mycobacteria* sps (e.g., *M. tuberculosis, M. avium, M. intracelluiar e, M. kansaii, M. gordonae*), *Staphylococcus aureus, Neisseria gonorrhoeae, Neisseria meningitides, Streptococcus pyogenes* (Group A *Streptococcus*), *Streptococcus agalactiae* (Group B *Streptococcus*), *Streptococcus* (*viridans* group), *Streptococcus faecalis, Streptococcus bovis, Streptococcus* (*anaerobic* sps.), *Streptococcus pneumoniae*, pathogenic *Campylobacter* sp., *Enterococcus* sp., *Haemophilus influenzae, Bacillus anthracis, Corynebacterium diphtheriae, corynebacterium* sp., *Erysipelothrix rhusiopathiae, Clostridium perfringers, Clostridium tetani, Enterobacter aerogenes, Klebsiella pneumoniae, Pasteurella multocida, Bacteroides* sp., *Fusobacterium nucleatum, Streptobacillus moniliformis, Treponema pallidium, Treponema pertenue, Leptospira, Rickettsia, Actinomyces israelli, Shigella* sps (e.g., *S. flexneri, S. sonnei, S. dysenteriae*), and *Salmonella* spp infections. Exemplary fungal infections include *Candida albicans, Candida glabrata, Aspergillus fumigatus, Aspergillus terreus, Cryptococcus neoformans, Histoplasma capsulatum, Coccidioides immitis, Blastomyces dermatitidis*, and *Chlamydia irachomatis* infections.

The oligonucleotide-lipid complex may be used herein as an antitumor, antiviral, antibacterial, antifungal, antiparasite, or anti-autoimmune agent in a variety of modalities. In a particular embodiment, the invention contemplates methods of using an oligonucleotide-lipid complex comprises contacting a population of diseased cells with a therapeutically effective amount of an oligonucleotide-lipid complex for a time period sufficient to inhibit or reverse disease.

In one embodiment, the contacting in vivo is accomplished by administering, by intravenous, intraperitoneal, subcutaneous, or intratumoral injection, a therapeutically effective amount of a physiologically tolerable composition comprising an oligonucleotide-lipid complex of this invention to a patient. The oligonucleotide-lipid complex can be administered parenterally by injection or by gradual infusion over time.

Therapeutic compositions comprising oligonucleotide-lipid complex are conventionally administered intravenously or subcutaneously, such as by injection of a unit dose, for example. The term "unit dose" when used in reference to a therapeutic composition refers to physically discrete units suitable as unitary dosage for the subject, each unit containing a predetermined quantity of active material calculated to produce the desired therapeutic effect in association with the required diluent, i.e., carrier, or vehicle.

The compositions are administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient required to be administered depend on the judgment of the practitioner and are peculiar to each individual. However, suitable dosage ranges for systemic application are disclosed herein and depend on the route of administration. Suitable regimes for initial and booster administration are also contemplated and are typified by an initial administration followed by repeated doses at one or more hour intervals by a subsequent injection or other administration. Exemplary multiple administrations are described herein and are particularly preferred to maintain continuously high serum and tissue levels of polypeptide. Alternatively, continuous intravenous infusion sufficient to maintain concentrations in the blood in the ranges specified for in vivo therapies are contemplated.

It is contemplated that an oligonucleotide of the invention can be administered systemically or locally to treat disease, such as to inhibit tumor cell growth or to kill cancer cells in cancer patients with locally advanced or metastatic cancers. They can be administered intravenously, intrathecally, subcutaneously, and/or intraperitoneally. They can be administered alone or in combination with anti-proliferative drugs. In one embodiment, they are administered to reduce the cancer load in the patient prior to surgery or other procedures. Alternatively, they can be administered after surgery to ensure that any remaining cancer (e.g., cancer that the surgery failed to eliminate) does not survive.

A therapeutically effective amount of an oligonucleotide is a predetermined amount calculated to achieve the desired effect, i.e., to inhibit the expression of a target protein. Thus, the dosage ranges for the administration of oligonucleotides of the invention are those large enough to produce the desired effect. The dosage should not be so large as to cause adverse side effects, such as hyperviscosity syndromes, pulmonary edema, congestive heart failure, neurological effects, and the like. Generally, the dosage will vary with age of, condition of, sex of, and extent of the disease in the patient and can be determined by one of skill in the art. The dosage can be adjusted by the individual physician in the event of any complication.

A composition of the present invention is preferably administered to a patient parenterally, for example by intravenous, intraarterial, intramuscular, intralymphatic, intraperitoneal, subcutaneous, intrapleural, or intrathecal injection, or may be used ex vivo. Preferred dosages are between 5-25 mg/kg. The administration is preferably repeated on a timed schedule until the cancer disappears or regresses, and may be in conjunction with other forms of therapy.

VII. PHARMACEUTICAL PREPARATIONS

A pharmaceutical composition comprising the liposomes will usually include a sterile, pharmaceutically acceptable carrier or diluent, such as water or saline solution.

Where clinical application of non-charged lipid component (e.g., in the form of a liposome) containing an oligonucleotide is undertaken, it will generally be beneficial to prepare the lipid complex as a pharmaceutical composition appropriate for the intended application. This will typically entail preparing a pharmaceutical composition that is essentially free of pyrogens, as well as any other impurities that could be harmful to humans or animals. One may also employ appropriate buffers to render the complex stable and allow for uptake by target cells.

The phrases "pharmaceutical or pharmacologically acceptable" refers to molecular entities and compositions that do not produce an adverse, allergic or other untoward reaction when administered to an animal, such as a human, as appropriate. The preparation of a pharmaceutical composition that contains at least one non-charged lipid component comprising an oligonucleotide or additional active ingredient will be known to those of skill in the art in light of the present disclosure, as exemplified by Remington: The Science and Practice of Pharmacy, 21st, 2005, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art. A pharmaceutically acceptable carrier is preferably formulated for administration to a human, although in certain embodiments it may be desirable to use a pharmaceutically acceptable carrier that is formulated for administration to a non-human animal but which would not be acceptable (e.g., due to governmental regulations) for administration to a human. Except insofar as any conventional carrier is incompatible with the active ingredient, its use in the therapeutic or pharmaceutical compositions is contemplated.

The actual dosage amount of a composition of the present invention administered to a patient or subject can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 μg/kg/body weight to about 100 mg/kg/body weight, about 5 microgram/kg/body weight to about 500 milligram/kg/body weight, etc., can be administered.

An oligonucleotide of the present embodiments may be administered in a dose of 1, 2, 3, 4, 5, 6, 7, 8, 9, 10, 15, 20, 25, 30, 40, 50, 60, 70, 80, 90, 100 or more μg of nucleic acid per dose. Each dose may be in a volume of 1, 10, 50, 100, 200, 500, 1000 or more μl or ml.

Solutions of therapeutic compositions can be prepared in water suitably mixed with a surfactant, such as hydroxypropylcellulose. Dispersions also can be prepared in glycerol, liquid polyethylene glycols, mixtures thereof and in oils. Under ordinary conditions of storage and use, these preparations contain a preservative to prevent the growth of microorganisms.

The therapeutic compositions of the present invention are advantageously administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain 10 mg, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like.

Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components the pharmaceutical composition are adjusted according to well-known parameters.

The therapeutic compositions of the present invention may include classic pharmaceutical preparations. Administration of therapeutic compositions according to the present invention will be via any common route so long as the target tissue is available via that route. This includes oral, nasal, buccal, rectal, vaginal or topical. Topical administration may be particularly advantageous for the treatment of skin cancers, to prevent chemotherapy-induced alopecia or other dermal hyperproliferative disorder. Alternatively, administration may be by orthotopic, intradermal, subcutaneous, intramuscular, intraperitoneal or intravenous injection. Such compositions would normally be administered as pharmaceutically acceptable compositions that include physiologically acceptable carriers, buffers or other excipients. For treatment of conditions of the lungs, aerosol delivery can be used. Volume of the aerosol is between about 0.01 ml and 0.5 ml.

An effective amount of the therapeutic composition is determined based on the intended goal. The term "unit dose" or "dosage" refers to physically discrete units suitable for use in a subject, each unit containing a predetermined-quantity of the therapeutic composition calculated to produce the desired responses discussed above in association with its administration, i.e., the appropriate route and treatment regimen. The quantity to be administered, both according to number of treatments and unit dose, depends on the protection or effect desired.

Precise amounts of the therapeutic composition also depend on the judgment of the practitioner and are peculiar to each individual. Factors affecting the dose include the physical and clinical state of the patient, the route of administration, the intended goal of treatment (e.g., alleviation of symptoms versus cure) and the potency, stability and toxicity of the particular therapeutic substance.

VIII. COMBINATION TREATMENTS

In certain embodiments, the compositions and methods of the present invention involve an inhibitory oligonucleotide, or oligonucleotide capable of expressing an inhibitor of gene expression, in combination with a second or additional therapy. The methods and compositions including combination therapies enhance the therapeutic or protective effect, and/or increase the therapeutic effect of another anti-cancer or anti-hyperproliferative therapy. Therapeutic and prophylactic methods and compositions can be provided in a combined amount effective to achieve the desired effect, such as the killing of a cancer cell and/or the inhibition of cellular hyperproliferation. This process may involve contacting the cells with both an inhibitor of gene expression and a second therapy. A tissue, tumor, or cell can be contacted with one or more compositions or pharmacological formulation(s) including one or more of the agents (i.e., inhibitor of gene expression or an anti-cancer agent), or by contacting the tissue, tumor, and/or cell with two or more distinct compositions or formulations, wherein one composition provides 1) an inhibitory oligonucleotide; 2) an anti-cancer agent, or 3) both an inhibitory oligonucleotide and an anti-cancer agent. Also, it is contemplated that such a combination therapy can be used in conjunction with a chemotherapy, radiotherapy, surgical therapy, or immunotherapy.

An inhibitory oligonucleotide may be administered before, during, after or in various combinations relative to an anti-cancer treatment. The administrations may be in intervals ranging from concurrently to minutes to days to weeks. In embodiments where the inhibitory oligonucleotide is provided to a patient separately from an anti-cancer agent, one would generally ensure that a significant period of time did not expire between the time of each delivery, such that the two compounds would still be able to exert an advantageously combined effect on the patient. In such instances, it is contemplated that one may provide a patient with the inhibitory oligonucleotide therapy and the anti-cancer therapy within about 12 to 24 or 72 h of each other and, more preferably, within about 6-12 h of each other. In some situations it may be desirable to extend the time period for treatment significantly where several days (2, 3, 4, 5, 6 or 7) to several weeks (1, 2, 3, 4, 5, 6, 7 or 8) lapse between respective administrations.

In certain embodiments, a course of treatment will last 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90 days or more. It is contemplated that one agent may be given on day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, and/or 90, any combination thereof, and another agent is given on day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, and/or 90, or any combination thereof. Within a single day (24-hour period), the patient may be given one or multiple administrations of the agent(s). Moreover, after a course of treatment, it is contemplated that there is a period of time at which no anti-cancer treatment is administered. This time period may last 1, 2, 3, 4, 5, 6, 7 days, and/or 1, 2, 3, 4, 5 weeks, and/or 1, 2, 3, 4, 5, 6, 7, 8, 9, 10, 11, 12 months or more, depending on the condition of the patient, such as their prognosis, strength, health, etc.

Various combinations may be employed. For the example below an inhibitory oligonucleotide therapy is "A" and an anti-cancer therapy is "B":

A/B/A B/A/B B/B/A A/A/B A/B/B B/A/A A/B/B/B
B/A/B/B B/B/B/A B/B/A/B A/A/B/B A/B/A/B A/B/B/A
B/B/A/A B/A/B/A B/A/A/B A/A/A/B B/A/A/A A/B/A/A
A/A/B/A

Administration of any compound or therapy of the present invention to a patient will follow general protocols for the administration of such compounds, taking into account the toxicity, if any, of the agents. Therefore, in some embodiments there is a step of monitoring toxicity that is attributable to combination therapy. It is expected that the treatment cycles would be repeated as necessary. It also is contemplated that various standard therapies, as well as surgical intervention, may be applied in combination with the described therapy.

In specific aspects, it is contemplated that a standard therapy will include chemotherapy, radiotherapy, immunotherapy, surgical therapy or gene therapy and may be employed in combination with the inhibitor of gene expression therapy, anticancer therapy, or both the inhibitor of gene expression therapy and the anti-cancer therapy, as described herein.

A. Chemotherapy

A wide variety of chemotherapeutic agents may be used in accordance with the present embodiments. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammaI1 and calicheamicin omegaI1); dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid; capecitabine; carboplatin, procarbazine, plicomycin, gemcitabien, navelbine, farnesyl-protein tansferase inhibitors, transplatinum, and pharmaceutically acceptable salts, acids, or derivatives of any of the above.

B. Radiotherapy

Other factors that cause DNA damage and have been used extensively include what are commonly known as γ-rays, X-rays, and/or the directed delivery of radioisotopes to tumor cells. Other forms of DNA damaging factors are also contemplated such as microwaves, proton beam irradiation (U.S. Pat. Nos. 5,760,395 and 4,870,287) and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing, for example, both agents are delivered to a cell in a combined amount effective to kill the cell or prevent it from dividing.

C. Immunotherapy

In the context of cancer treatment, immunotherapeutics, generally, rely on the use of immune effector cells and molecules to target and destroy cancer cells. Trastuzumab (Herceptin™) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells. The combination of therapeutic modalities, i.e., direct cytotoxic activity and inhibition or reduction of ErbB2 would provide therapeutic benefit in the treatment of ErbB2 overexpressing cancers.

Another immunotherapy could also be used as part of a combined therapy with gen silencing therapy discussed above. In one aspect of immunotherapy, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155. An alternative aspect of immunotherapy is to combine anticancer effects with immune stimulatory effects. Immune stimulating molecules also exist including: cytokines such as IL-2, IL-4, IL-12, GM-CSF, gamma-IFN, chemokines such as MIP-1, MCP-1, IL-8 and growth factors such as FLT3 ligand. Combining immune stimulating molecules, either as proteins or using gene delivery in combination with a tumor suppressor has been shown to enhance anti-tumor effects. Moreover, antibodies against any of these compounds can be used to target the anti-cancer agents discussed herein.

Examples of immunotherapies currently under investigation or in use are immune adjuvants e.g., *Mycobacterium bovis, Plasmodium falciparum*, dinitrochlorobenzene and aromatic compounds (U.S. Pat. Nos. 5,801,005 and 5,739, 169; Hui and Hashimoto, 1998; Christodoulides et al., 1998), cytokine therapy, e.g., interferons α, β and γ; IL-1, GM-CSF and TNF (Bukowski et al., 1998; Davidson et al., 1998; Hellstrand et al., 1998) gene therapy, e.g., TNF, IL-1, IL-2, p53 (Qin et al., 1998; Austin-Ward and Villaseca, 1998; U.S. Pat. Nos. 5,830,880 and 5,846,945) and monoclonal antibodies, e.g., anti-ganglioside GM2, anti-HER-2, anti-p185 (Pietras et al., 1998; Hanibuchi et al., 1998; U.S. Pat. No. 5,824,311). It is contemplated that one or more anti-cancer therapies may be employed with the gene silencing therapies described herein.

In active immunotherapy, an antigenic peptide, polypeptide or protein, or an autologous or allogenic tumor cell composition or "vaccine" is administered, generally with a distinct bacterial adjuvant (Ravindranath and Morton, 1991; Morton et al., 1992; Mitchell et al., 1990; Mitchell et al., 1993).

In adoptive immunotherapy, the patient's circulating lymphocytes, or tumor infiltrated lymphocytes, are isolated in vitro, activated by lymphokines such as IL-2 or transduced with genes for tumor necrosis, and readministered (Rosenberg et al., 1988; 1989).

D. Surgery

Approximately 60% of persons with cancer will undergo surgery of some type, which includes preventative, diagnostic or staging, curative, and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue.

Upon excision of part or all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

E. Other Agents

It is contemplated that other agents may be used in combination with certain aspects of the present embodiments to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present embodiments to improve the treatment efficacy.

IX. KITS AND DIAGNOSTICS

In various aspects of the invention, a kit is envisioned containing therapeutic agents and/or other therapeutic and delivery agents. In some embodiments, the present invention contemplates a kit for preparing and/or administering a therapy of the invention. The kit may comprise reagents capable of use in administering an active or effective agent (s) of the invention. Reagents of the kit may include at least one inhibitor of gene expression, one or more lipid component, one or more anti-cancer component of a combination therapy, as well as reagents to prepare, formulate, and/or administer the components of the invention or perform one or more steps of the inventive methods.

In some embodiments, the kit may also comprise a suitable container means, which is a container that will not react with components of the kit, such as an eppendorf tube, an assay plate, a syringe, a bottle, or a tube. The container may be made from sterilizable materials such as plastic or glass.

The kit may further include an instruction sheet that outlines the procedural steps of the methods, and will follow substantially the same procedures as described herein or are known to those of ordinary skill.

X. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Method of Manufacturing Liposomal p-Ethoxy Antisense Drug Product

The liposomal p-ethoxy antisense drug product is composed of two cGMP products, both of which have a FDA-required Certificate of Analysis with FDA-approved release criteria. The raw materials, solvents, and final drug product are described herein. When manufactured, the drug product is a lyophilized crystal or powder of amber or white color that comprises the following materials: oligonucleotide (e.g., p-ethoxy antisense drug substance), neutral lipids (e.g., DOPC), and surfactant (e.g., polysorbate 20). In preparation for administration to a patient, normal saline is added to the vial, at which time liposomes are formed with the p-ethoxy antisense incorporated into the interior.

P-Ethoxy Antisense Drug Substance.

Specific physical properties (e.g., solubility and hydrophobicity, which then affect drug product solubility in saline, incorporation of oligo into liposomes, and liposome particle size) of the finished product can be defined using a predetermined p-ethoxy and phosphodiester amidite raw material mix during production of the p-ethoxy antisense drug substance. While loss of the p-ethoxy backbone group randomly occurs during oligonucleotide manufacturing resulting in phosphodiester bonds at those linkages, that loss may not generate the preferred ratio of p-ethoxy:phosphodiester backbone linkage within the oligonucleotide. In this case, the mix of p-ethoxy and phosphodiester amidite raw material supplements the expected value of p-ethoxy backbone deletions, thus generating an oligonucleotide with the desired ratio. Increasing the number of p-ethoxy molecules in the backbone of the oligonucleotide causes the molecule to be more hydrophobic (which results in larger liposome particles; Table 1), less polar, and less soluble (Table 2). Methods of testing the charge-neutral, hydrophobic p-ethoxy drug substance include mass spectrometry to determine the distribution of oligonucleotide lengths and assays to determine the solubility of drug substance, which for practical purposes for solubility is a visual inspection of the drug product reconstituted in saline. As the oligonucleotide becomes less soluble due to a greater number of p-ethoxy backbone linkages the reconstituted solution becomes whiter until particulates form as hydrophobicity becomes too high.

TABLE 1

Liposome Particle Size Variability with Antisense Backbone Composition

| Experiment | Engineered Antisense Backbone | Post-Manufacturing Backbone Ethyl Deletion | | Particle Size Characteristics: Cumulative Distribution Function | | |
|---|---|---|---|---|---|---|
| | | Principal Peak | Composite Deletion | 90% Value (nm) ** | 50% Value (nm) | 300 nm Value (%) |
| 1 | 3 amidite substitution | −6 | −5.67 | 2130 | 911 | 15.30 |
| 2 | 3 amidite substitution | −6 | −5.67 | 2420 | 1004 | 15.50 |
| 3 | 3 amidite substitution | −6 | −6.12 | 3682 | 943 | 15.50 |
| 4 | 3 amidite substitution | −7 | −6.66 | 3805 | 978 | 14.60 |
| 5 | 100% p-ethoxy | −5 | −5.66 | 3924 | 976 | 16.00 |
| 6 | 2 amidite substitution | −5 | −5.32 | 4387 | 1888 | 11.60 |
| 7[a] | 100% | −4 | −4.22 | 5057 | 1131 | 17.70 |
| 8 | 100% p-ethoxy | −4 | −4.52 | 5659 | 1359 | 10.00 |
| 9[b] | 100% p-ethoxy | −4 | −4.38 | 7571 | 1909 | 2.60 |
| 10[c] | 100% p-ethoxy | −4 | −4.38 | 7994 | 1653 | 14.40 |

**Drug product release criteria is for 90% of the liposome particles to be less than or equal to 5000 nm.
[a]This lot was discarded due to poor solubility; specifically, antisense particles in the reconstituted solution.
[b]This lot had lower DMSO and tBA volume with 2 mg antisense in a 20 mL vial, which added an additional component to liposome enlargement.
[c]This lot was not released because it failed the particle size release spec.

TABLE 2

Liposome Particle Solubility with Antisense Backbone Composition

| Experiment | Engineered Antisense Backbone | Post-Manufacturing Backbone Ethyl Deletion | | Drug Solubility | |
|---|---|---|---|---|---|
| | | Principal Peak | Composite Deletion | Visual Observation** | Solubility Assessment |
| 1 | 3 amidite substitution | −6 | −5.67 | skim milk solution | good |
| 2 | 3 amidite substitution | −6 | −5.67 | skim milk solution | good |
| 3 | 3 amidite substitution | −6 | −6.12 | skim milk solution | good |
| 4 | 3 amidite substitution | −7 | −6.66 | skim milk solution | good |
| 5 | 100% p-ethoxy | −5 | −5.66 | skim milk solution | good |
| 6 | 2 amidite substitution | −5 | −5.32 | skim milk solution | good |
| 7 | 100% p-ethoxy | −4 | −4.52 | white solution | pass |
| 8[b] | 100% p-ethoxy | −4 | −4.38 | white solution | pass |
| 9[c] | 100% p-ethoxy | −4 | −4.38 | white solution | pass |
| 10[a] | 100% p-ethoxy | −4 | −4.22 | white solution particles | fail |

**If the drug product sample has particles the lot will be rejected
[a]This lot was discarded due to poor solubility; specifically, antisense particles in the reconstituted solution.
[b]This lot had lower DMSO and tBA volume with 2 mg antisense in a 20 mL vial, which added an additional component to liposome enlargement.
[c]This lot was not released because it failed the particle size release spec.

Formulation, Filtration, and Lyophilization of Liposomal p-Ethoxy Antisense Drug Product.

One gram (1 g) of pE oligos are dissolved in DMSO at a ratio of 10 mg oligonucleotide per 1 mL DMSO. Next, DOPC is added to tert-butyl alcohol at a ratio of 1 g DOPC per 1719 mL of tert-butyl alcohol. The oligo and DOPC are combined and mixed at a ratio of 1 g oligonucleotide per 2.67 g DOPC. Then, 20 mL of a 0.835% (v/v) solution of polysorbate 20 is added to the mixture resulting in a final concentration of 0.039 mg/mL. The solution is passed through a sterile filter prior to dispensing into glass vials for lyophilization.

The effect of the surfactant on liposome particle size was determined by titrating the amount of surfactant (Table 3). In the absence of polysorbate 20, only 2.8% of the particles had a diameter of 300 nm or less. In the presence of 1× polysorbate 20 (about 5% of the total liposomal p-ethoxy antisense drug product), 12.5% of the particles had a diameter of 300 nm or less. With the addition of 3×-10× polysorbate 20, around 20% of the particles had a diameter of 300 nm or less. Thus an increase in surfactant from 1× to 3× results in a decrease in particle size.

TABLE 3

Liposome Particle Size Variability with Surfactant

| Experiment | Amount of Surfactant | Particle Size Characteristics: Cumulative Distribution Function | | |
|---|---|---|---|---|
| | | 50% Value | 90% Value** | 300 nm Value |
| 1 | 0× | 5301 nm | 10719 nm | 2.8% |
| 2 | 1× | 1053 nm | 4054 nm | 12.5% |
| 3 | 3× | 785 nm | 2926 nm | 19.1% |
| 4 | 5× | 721 nm | 2691 nm | 21.9% |
| 5 | 10× | 734 nm | 2937 nm | 21.4% |

**Drug product release criteria is for 90% of the liposome particles to be less than or equal to 5000 nm.

Preparation of Liposomal p-Ethoxy Antisense Drug Product for Administration.

The lyophilized preparation was hydrated with normal saline (0.9%/10 mM NaCl) at a final oligo concentration of 10-5000 μM. The liposomal-p-ethoxy oligos were mixed by hand shaking.

Example 2—Methods of Testing Liposomal p-Ethoxy Antisense Drug Product

Visual Inspection of Manufactured Drug Product:

After manufacturing, a sample vial containing drug product is selected and visually inspected. The absence of liquid is mandatory, and then amber crystals at the bottom of the vial are acceptable, and increasing in acceptance to a white, flocculated powder or appearance, the best result. The white appearance indicates a better drying process, with a high surface area to mass ratio, which is very conducive to reconstitution for use.

Visual Inspection of Reconstituted Drug Ready for Patient IV:

Normal saline is added to a vial containing the manufactured Liposomal P-ethoxy Antisense Drug Product and shaken to reconstitute into a solution with the drug crystal or powder completely dissolved. Three main observations are made: 1) that the crystal or powder is completely dissolved, 2) there are no white clumps of undissolved material, and 3) the appearance is a milky white or skim milk appearance. The bluer the appearance of the reconstituted liquid, the better, as this signals a smaller liposome particle size that reflects light in the blue spectrum.

Mass Spectrometry:

Mass spectrometry (mass spec) is used to display the profile of the various masses in a sample. When p-ethoxy antisense material is produced, a mass spec is run on the sample. The result shows peaks of material present on a grid that has increasing mass on the "x" axis to the right, and relative mass abundance on the "y" axis increasing upward. The profile from a sample is analyzed to determine the relative quantity of p-ethoxy backbones in the p-ethoxy sample, recognizing that the profile of peaks represents (starting farthest to the right), full length material with all backbones comprised of the p-ethoxy linkage, the next peak moving left a full length with one backbone with a p-ethoxy deletion (and therefore, the ethyl being knocked off and the result being a normal phosphodiester backbone linkage), and continuing. The mass spec pattern shifted to the right represents a p-ethoxy sample having more p-ethoxy backbones, and therefore having the properties of being more hydrophobic and less soluble; and likewise, shifted to the left having the opposite effects. Inspection of the mass spec chart of a sample also can be used to determine if filtration during manufacturing produces any adverse effects on oligonucleotide composition present in the filtered drug product.

UV Testing:

Ultraviolent light testing is used to determine the mass of oligonucleotide present in a sample. Oligonucleotides absorb light in the 260 nanometer range. As a result, UV testing of the finished reconstituted drug product has come to be used as a method in determining the quantity of oligonucleotide drug substance in a vial of drug product. In terms of manufacturing development and innovations, UV testing was used to determine if there were problems experienced during filtration in manufacturing or poor solubility of the p-ethoxy antisense drug substance, resulting in less oligonucleotide in solution and therefore a lower UV reading. The method will be validated and likely become part of the final product release testing.

Liposome Particle Size:

A vial of finished drug product is reconstituted and tested for liposome particle size. The result is often a roughly normal distribution, having a central point, tails and average values or a roughly normal distribution of the majority of the particles and smaller, secondary peaks of the smaller liposomes particles resulting from second-order particle formation effects. It is important that liposome particles not be too large, as they may create adverse effects in patients (for example, create blood flow problems in smaller blood vessels in the lungs). As a result, the drug product release criteria include that particle size testing show that 90% of liposomes be about 5 microns or less in size. In addition, smaller liposomes are preferred because they will have better uptake into cells, and secondly, smaller liposomes can penetrate vascular pores, thereby allowing the liposomes to penetrate inside tumors, increasing treatment effectiveness of a Liposomal P-ethoxy Antisense Drug Product.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,659,774
U.S. Pat. No. 4,816,571
U.S. Pat. No. 4,870,287
U.S. Pat. No. 4,959,463
U.S. Pat. No. 5,141,813
U.S. Pat. No. 5,214,136
U.S. Pat. No. 5,223,618
U.S. Pat. No. 5,264,566
U.S. Pat. No. 5,378,825
U.S. Pat. No. 5,428,148
U.S. Pat. No. 5,446,137
U.S. Pat. No. 5,466,786
U.S. Pat. No. 5,470,967
U.S. Pat. No. 5,539,082
U.S. Pat. No. 5,554,744
U.S. Pat. No. 5,574,146
U.S. Pat. No. 5,602,240
U.S. Pat. No. 5,602,244
U.S. Pat. No. 5,610,289
U.S. Pat. No. 5,614,617
U.S. Pat. No. 5,623,070
U.S. Pat. No. 5,652,099
U.S. Pat. No. 5,670,663
U.S. Pat. No. 5,672,697
U.S. Pat. No. 5,681,947
U.S. Pat. No. 5,700,922
U.S. Pat. No. 5,705,629
U.S. Pat. No. 5,708,154
U.S. Pat. No. 5,714,331
U.S. Pat. No. 5,714,606
U.S. Pat. No. 5,719,262
U.S. Pat. No. 5,736,336
U.S. Pat. No. 5,739,169
U.S. Pat. No. 5,760,395
U.S. Pat. No. 5,763,167
U.S. Pat. No. 5,766,855
U.S. Pat. No. 5,773,571
U.S. Pat. No. 5,777,092
U.S. Pat. No. 5,786,461
U.S. Pat. No. 5,792,847
U.S. Pat. No. 5,801,005
U.S. Pat. No. 5,824,311
U.S. Pat. No. 5,830,880
U.S. Pat. No. 5,846,945
U.S. Pat. No. 5,855,911
U.S. Pat. No. 5,858,988
U.S. Pat. No. 5,859,221
U.S. Pat. No. 5,872,232
U.S. Pat. No. 5,886,165
U.S. Pat. No. 5,891,625
U.S. Pat. No. 5,908,845
Austin-Ward and Villaseca, Revista Medica de Chile, 126(7):838-845, 1998.
Bailey and Sullivan, Biochimica. Biophys. Acts., 239-252, 2000.
Bangham et al., J. Mol. Biol, 13(1):253-259, 1965.
Bukowski et al., Clinical Cancer Res., 4(10):2337-2347, 1998.
Christodoulides et al., Microbiology, 144(Pt 11):3027-3037, 1998.
Davidson et al., J. Immunother., 21(5):389-398, 1998.
Deamer and Uster, In: Liposome Preparation: Methods and Mechanisms, Ostro (Ed.), Liposomes, 1983.
Dokka et al., Pharm Res, 17: 521-25, 2000.
duBois et al., J Clin Oncol, 17: 46-51, 1999.
Dubey et al, J. Drug Target, 12:257-264, 2004.
Duxbury et al., Biochem. Biophys. Res. Commun., 311:786-792, 2003.
Duxbury et al., Oncogene, 23:1448-1456, 2004.
Egholm et al., Nature, 365(6446):566-568, 1993.
Elbashir et al., Nature, 411 (6836):494-498, 2001.
European Appln. 01219
European Appln. 266,032
Farhood et al., Biochim. Biophys. Act, 289-295, 1995.
Fire et al., Nature, 391(6669):806-811, 1998.
Flenniken et al., Dev. Biol., 179:382-401, 1996.
Froehler et al., Nucleic Acids Res., 14(13):5399-5407, 1986.
Gabizon, Cancer Invest., 19:424-436, 2001.
Ghosh and Bachhawat, In: Liver Diseases, Targeted Diagnosis and Therapy Using Specific Receptors and Ligands, Wu et al. (Eds.), Marcel Dekker, NY, 87-104, 1991.
Gregoriadis, In: Drug Carriers in Biology and Medicine, Gregoriadis (Ed.), 287-341, 1979.
Gutierrez-Puente et al., J. Pharmacol. Exp. Ther., 291:865-869, 1999.
Halder et al., Clinical Cancer Research, 11: 8829-36, 2005.
Han et al., Ann Surg Oncol, 4:264-268, 1997.
Hanibuchi et al., Int. J. Cancer, 78(4):480-485, 1998.
Hannon and Rossi, Nature, 431:371-378, 2004.
Hassani et al., J. Gene Med., 7(2):198-207, 2005.
Hecker et al., Cancer Research, 62:2699-2707, 2002.
Hellstrand et al., Acta Oncologica, 37(4):347-353, 1998.
Hortobagyi et al., J. Clin. Oncol., 19:3422-3433, 2001.
Hsia et al., J Cell Biol, 160:753-67, 2003.
Hui and Hashimoto, Infection Immun., 66(11):5329-5336, 1998.
Jackson et al., Nat. Biotechnol., 21:635-637, 2003.
Jemal et al, CA Cancer J. Clin., 55(1):10-30, 2005.
Judson et al., Cancer, 86: 1551-56, 1999.
Kaneda et al., Science, 243:375-378, 1989.
Kato et al., J. Biol. Chem., 266:3361-3364, 1991.
Kim et al., Nat. Biotechnol., 22:321-325, 2004.
Kinch et al., Clin. Exp. Metastasis, 20:59-68, 2003.
Klein et al., Gastroenterology, 125:9-18, 2003.
Kohno et al., Int J Cancer, 97:336-43, 2002.
Kornberg and Baker, DNA Replication, 2nd Ed., Freeman, San Francisco, 1992.
Kornberg et al., Invest Opthalmol Vis Sci, 45:4463-69, 2004.
Kornberg, Head Neck, 20: 634-639, 1998.
Kostarelos et al., Int J Cancer, 112: 713-21, 2004.
Krasnici et al., Int. J. Cancer, 105(4):561-567, 2003.
Landen, Cancer Res, 65: 6910-18, 2005.
Langley et al., Cancer Research, 63: 2971-76, 2003.
Lewis et al., Cell, 115:787-798, 2003.
Lewis et al., Nat. Genet., 32:107-108, 2002.
Lori et al., Am. J. Pharmacogenomics, 2:245-252, 2002.
Matsuda et al., Proc. Natl. Acad. Sci. USA, 101:16-22, 2004.
McCaffrey et al., Nature, 418:38-39, 2002.
McGuire et al., New England Journal of Medicine, 334:1-6, 1996.
McLean et al., Expert Opin Pharmacother, 4: 227-34, 2003.
Miller et al., Biochemistry, 37(37):12875-83, 1998.
Mitchell et al., Ann. NY Acad. Sci., 690:153-166, 1993.
Mitchell et al., J. Clin. Oncol., 8(5):856-869, 1990.
Mitra et al., Nature Reviews Molecular Cell Biology, 6: 56-68, 2005.
Mitra et al., Proc Am Assoc Cancer Res, 2005.
Morton et al., Arch. Surg., 127:392-399, 1992.
Nemoto et al., Pathobiology, 65:195-203, 1997.
Nicolau et al., Methods Enzymol., 149:157-176, 1987.
Noblitt et al., Cancer Gene Ther., 11:757-766, 2004.
Ogawa et al, Oncogene, 19:6043-6052, 2000.

Owens et al., Cancer Res, 55:2752-2755, 1995.
Park et al., Cancer Lett., 118:153-160, 1997.
PCT Appln. WO 92/20702
PCT Appln. WO02/100435A1
PCT Appln. WO03/015757A1
PCT Appln. WO04/002453A1
PCT Appln. WO04029213A2
Pietras et al., Oncogene, 17(17):2235-2249, 1998.
Qin et al., Proc. Natl. Acad. Sci. USA, 95(24):14411-14416, 1998.
Ravindranath and Morton, Intern. Rev. Immunol., 7: 303-329, 1991.
Reich et al., Mol. Vis., 9:210-216, 2003.
Remington's Pharmaceutical Sciences, 18th Ed. Mack Printing Company, 1289-1329, 1990.
Rosenberg et al., Ann. Surg. 210(4):474-548, 1989.
Rosenberg et al., N. Engl. J. Med., 319:1676, 1988.
Ryther et al., Gene Ther., 12(1):5-11, 2004.
Sambrook et al., In: Molecular cloning, Cold Spring Harbor Laboratory Press, Cold Spring Harbor, N.Y., 2001.
Schaller and Parsons, Trends in Cell Biology, 3:258-62, 1993.
Schaller et al., Mol Biol Cell, 10:3489-3505, 1999.
Schaller, Biochim Biophys Acta, 1540:1-21, 2001.
Schaller, J Endocrinol, 150:1-7, 1996.
Schaller, Trends Cell Biol, 3:258-262, 1993.
Scheit, In: Synthesis and Biological Function, Wiley-Interscience, NY, 171-172, 1980.
Schlaepfer and Hunter, Trends in Cell Biology, 8: 151-57, 1998.
Schlaepfer et al., Prog Biophys Mol Biol, 71: 435-78, 1999.
Sein et al., Oncogene, 19: 5539-42, 2000.
Sheta et al., J Natl Cancer inst, 92: 1065-73, 2000.
Shibata et al., Cancer Res, 58: 900-903, 1998.
Sieg et al., Nat Cell Biol, 2:249-56, 2000.
Sioud and Sorensen, Biochem. Biophys. Res. Comm., 312: 1220-1225, 2003.
Siwak et al., Clin Cancer Res, 8: 955-56, 2002.
Sledz et al., Nat. Cell Biol., 5:834-839, 2003.
Song et al., Nature Med. 9:347-351, 2003.
Sonoda et al., Journal of Biological Chemistry, 275:16309-15, 2000.
Sood et al., Am J Pathol, 165:1087-1095, 2004.
Sood et al., Cancer Biology & Therapy, 1: 511-17, 2002.
Sorensen et al., J. Mol. Biol., 327:761-66, 2003.
Soutschek et al., Nature, 432:173-178, 2004.
Spagnou et al., Biochemistry, 43:13348-13356, 2004.
Sulman et al., Genomics, 40:371-374, 1997.
Szoka and Papahadjopoulos, Proc. Natl. Acad. Sci. USA, 75:4194-4198, 1978.
Thaker et al., 36th Annual Meeting of the Society of Gynecologic Oncologists, Miami, Fla., 2005.
Thaker et al., Clin. Cancer Res., 10:5145-5150, 2004.
Thurston et al., J. Clin. Invest., 101(7):1401-1413, 1998.
Uchida et al., Mol. Ther., 10:162-171, 2004.
Voskoglou-Nomikos et al., Clin. Cancer Res., 9:4227-4239, 2003.
Walker-Daniels et al., Prostate, 41:275-80, 1999.
Wianny et al., Nat. Cell Biol., 2:70-75, 2000.
Wong et al., Gene, 10:87-94, 1980.
Xia et al., Nat. Biotechnol, 20:1006-10, 2002.
Yang et al., Oncogene, 22:5694-701, 2003.
Zelinski et al., Cancer Res., 61:2301, 2001.
Zhang et al., J. Biol. Chem., 279:10677-684, 2004.

What is claimed is:

1. A method of treating a subject with a cancer, an autoimmune disease, or an infectious disease comprising administering to the subject a therapeutically effective amount of a pharmaceutical composition comprising a population of oligonucleotides, phospholipids, and a pharmaceutically acceptable carrier, wherein oligonucleotides of the population are composed of nucleoside molecules linked together through phosphate backbone linkages, wherein at least one of the phosphate backbone linkages in each oligonucleotide is a p-ethoxy backbone linkage, wherein no more than 80% of the phosphate backbone linkages in each oligonucleotide are p-ethoxy backbone linkages, and wherein the oligonucleotides and phospholipids form an oligonucleotide-lipid complex.

2. The method of claim 1, wherein 50% to 80% of the phosphate backbone linkages are p-ethoxy backbone linkages.

3. The method of claim 1, wherein 20% to 50% of the phosphate backbone linkages are phosphodiester backbone linkages.

4. The method of claim 1, wherein the oligonucleotides of the population have an average size of 18 nucleotides, wherein no more than 14 of the phosphate backbone linkages in each oligonucleotide is a p-ethoxy backbone linkage.

5. The method of claim 1, wherein the population of oligonucleotides comprises a single species of oligonucleotides.

6. The method of claim 1, wherein the oligonucleotides of the population inhibit the expression of at least one oncogenic protein, infectious agent protein, or self-antigen.

7. The method of claim 1, wherein the phospholipids are neutral phospholipids.

8. The method of claim 7, wherein the neutral phospholipids are phosphatidylcholines.

9. The method of claim 1, wherein the phospholipids and oligonucleotides are present at a molar ratio of from about 5:1 to about 100:1.

10. The method of claim 1, wherein the oligonucleotide-lipid complex is further defined as a population of liposomes.

11. The method of claim 10, wherein at least 90% of the liposomes are less than 5 microns in diameter.

12. The method of claim 1, wherein the subject is a human.

13. The method of claim 1, wherein the cancer is a bladder, blood, pancreas, bone, bone marrow, brain, breast, colon, esophagus, stomach, head and neck, kidney, liver, lung, prostate, skin, testis, tongue, ovary, or uterine cancer.

14. The method of claim 1, wherein the autoimmune disease is Lupus erythematosis, Sjogren's disease, Crohn's disease, diabetes mellitus, multiple sclerosis, or rheumatoid arthritis.

15. The method of claim 1, wherein the infectious disease is a bacterial infection, fungal infection, viral infection, or parasitic infection.

16. The method of claim 1, wherein the composition is administered subcutaneously, intravenously, or intraperitoneally.

17. The method of claim 1, further comprising administering at least a second anticancer therapy to the subject.

18. The method of claim 17, wherein the second anticancer therapy is a surgical therapy, chemotherapy, radiation therapy, cryotherapy, hormone therapy, immunotherapy, anti-viral therapy, immune suppression therapy, anti-bacterial therapy, antiparasite therapy, anti-fungal therapy, or cytokine therapy.

19. The method of claim 1, wherein the oligonucleotides of the population are not chimeric.

20. The method of claim 1, wherein the phosphodiester backbone linkages in each of the oligonucleotides of the population are randomly spaced throughout each oligonucleotide.

* * * * *